(12) United States Patent
Koshti et al.

(10) Patent No.: US 11,332,564 B2
(45) Date of Patent: May 17, 2022

(54) METHOD TO PRODUCE STIMULI SENSITIVE UV ABSORBING POLYMERS

(71) Applicant: GALAXY SURFACTANTS LTD, Maharashtra (IN)

(72) Inventors: Nirmal Koshti, Piscataway, NJ (US); Prabhu Charan Kurakula Thulasiramreddy, Andhra Pradesh (IN)

(73) Assignee: GALAXY SURFACTANTS LTD., Maharashtra (IN)

( * ) Notice: Subject to any disclaimer, the term of this patent is extended or adjusted under 35 U.S.C. 154(b) by 103 days.

(21) Appl. No.: 16/998,016

(22) Filed: Aug. 20, 2020

(65) Prior Publication Data

US 2021/0301052 A1 Sep. 30, 2021

(30) Foreign Application Priority Data

Mar. 19, 2020 (IN) .............................. 202021011960

(51) Int. Cl.
*C08F 220/56* (2006.01)
*A61K 8/81* (2006.01)
(Continued)

(52) U.S. Cl.
CPC .......... *C08F 220/56* (2013.01); *A61K 8/8117* (2013.01); *A61K 8/8158* (2013.01);
(Continued)

(58) Field of Classification Search
CPC .... C08F 220/54; C08F 20/56; C08F 2800/10; C08F 212/18; C08F 212/26
See application file for complete search history.

(56) References Cited

U.S. PATENT DOCUMENTS

| 4,009,201 | A | * | 2/1977 | Steckler | .................. | C08F 20/34 560/222 |
| 4,308,335 | A | * | 12/1981 | Yamamoto | ............... | G03C 8/56 428/515 |

(Continued)

OTHER PUBLICATIONS

Bos, et al., "The 500 Dalton rule for the skin penetration of chemical compounds and drugs" Exp Dermatol 2000: 9: 165-169.

(Continued)

*Primary Examiner* — Robert C Boyle
(74) *Attorney, Agent, or Firm* — Cantor Colburn LLP

(57) ABSTRACT

Eco-friendly aqueous synthesis of substantive, UV-absorbing, cationic polymers with 'inverse temperature dependent solubility' are described in the present invention. These polymers are water-soluble at ambient temperature and water-resistant at temperature of human body as well as in the presence of electrolytes. This property makes these polymers useful for personal care products that are designed for protecting skin and hair from damages of UV radiation. The invention relates to aqueous synthesis of polymers of Formula I wherein, ArCO is an UV absorbing moiety selected from 2-cyano-3,3-diphenyl acryloyl, and (Continued)

p-methoxy cinnamoyl, $R_1$ is selected from H and $C_1$-$C_3$ alkyl group, and $R_2$ is selected from $C_1$-$C_3$ alkyl group, m and n are integers and a ratio of m to n is 40:5 to 40:1.

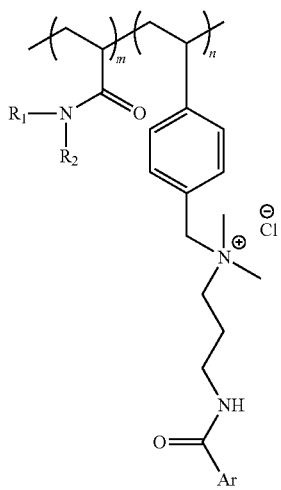

Formula I

4 Claims, 3 Drawing Sheets

(51) Int. Cl.
C08F 8/32 (2006.01)
C08F 212/14 (2006.01)
A61Q 17/04 (2006.01)
(52) U.S. Cl.
CPC ............... *A61Q 17/04* (2013.01); *C08F 8/32* (2013.01); *C08F 212/18* (2020.02)

(56) References Cited

U.S. PATENT DOCUMENTS

| | | |
|---|---|---|
| 5,476,913 A * | 12/1995 | Kourai .................. A01N 33/12 526/310 |
| 7,087,692 B2 | 8/2006 | Koshti et al. |
| 7,597,825 B2 | 10/2009 | Bonda et al. |
| 7,915,330 B2 | 3/2011 | Bonda et al. |
| 2004/0101498 A1 * | 5/2004 | Koshti ..................... C08F 8/44 424/59 |

OTHER PUBLICATIONS

Dondi, et al., "Interactions between different solar UMB/UVA filters contained in commerical suncreams and consequent loss of UV protection" Photochemical & Photobiological Sciences, 2006, 5, 835-843.
Downs, et al., "Toxicopathological Effects of the Sunscreen UV Filter, Oxybenzone (Benzophenone-3), on Coral Planulae and Cultured Primary Cells and Its Invironmental Contamination in Hawaii and the U.S. Virgin Islands" Arch Environ Contam Toxicol (2016) 70:265-288 DOI 10.1007/s00244-015-0227-7.
Liu, et al., "Synthesis of Thermal Phase Separating Reactive Polymers and Their Applications in Immobilized Enzymes" Polymer Journal, vol. 25, No. 6, pp. 561-567 (1993).
Schmaljohann, D., "Thermo- and pH-responsive polymers in drug delivery" Advanced Drug Delivery Reviews 58 (2006) 1655-1670.
The Commission of the European Communities, "Commission Recommendation of Sep. 22, 2006 on the efficacy of sunscreen products and the claims made relating thereto" Official Journal of the European Union, document No. C(2006) 4089, L 265/39-265/43.
Zraick, K., "Key West Bans Sunscreen Containing Chemicals Believed to Harm Coral Reefs" downloaded on Aug. 20, 2020; https://www.nytimes.com/2019/02/07/us/sunscreen-coral-reef-key-west.html.

* cited by examiner

METHOD TO PRODUCE STIMULI SENSITIVE UV ABSORBING POLYMERS

FIELD OF INVENTION

The invention relates to water-soluble, cationic, heat and electrolyte sensitive UV-absorbing polymers for personal care. More particularly, this invention relates to eco-friendly aqueous process of manufacture of these UV-absorbing polymers containing methoxy cinnamoyl and/or cyano diphenyl acryloyl moieties. The polymers produced by the green synthesis are not only substantive to hair and skin, but they also exhibit reversibly switchable solubility in water by stimuli of either temperature and/or salt and hence are useful for personal care applications.

BACKGROUND AND PRIOR ART

Salt and heat sensitive, UV light absorbing polymers (U.S. Pat. No. 7,087,692) that are substantive to hair and skin surface, have been reported in early 2000's by Koshti et al. This patent describes the use of poly N-isopropyl acrylamide (PNIPAM) backbone for the property of reversibly switchable sensitivity of these polymers towards heat and salt. The lower critical solution temperature (LCST) in water of UV-absorbing polymers of this patent is around 30° C. to 35° C. This means the polymers are soluble in water below 30° C. Above this temperature of 30° C., the PNIPAM based polymers coagulate, lose their solubility in water and completely precipitate out from aqueous solution. Koshti et al. copolymerized N-isopropyl acrylamide with vinyl benzyl chloride (Formula VI) in such a way that it retains the basic property of lower critical solution temperature (LCST) in water around 30° C. The copolymer thus obtained was further functionalized by reacting with UV absorbing chromophores like p-methoxy cinnamoyl with end tertiary amino group exploiting the reactivity of benzylic chloride. Thus, the copolymers made this way show the necessary LCST in water and ability to adhere to the hair and skin surface due the of the quaternary ammonium centre as depicted in the scheme 1 below.

Scheme 1

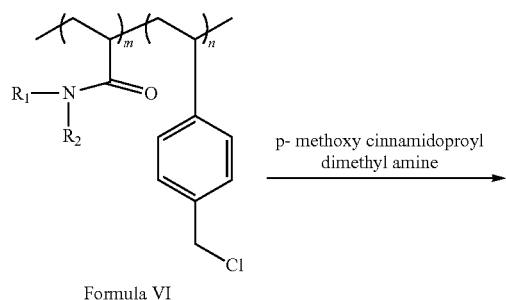

Formula VI p- methoxy cinnamidoproyl dimethyl amine

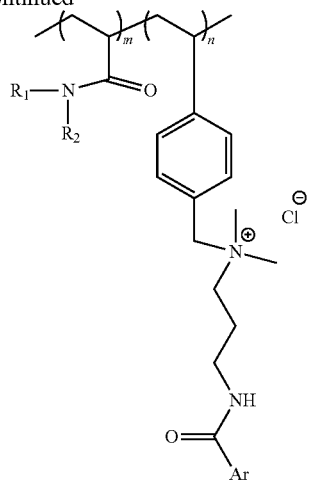

Formula I a

These water-soluble UV-absorbing polymers are substantive to hair and skin due to the attractive interaction between negatively charged surface of skin and hair with positively charged UV-absorbing polymer. Their application on to the surface of the skin or hair can be via any personal care formulation like a cream or a lotion or a shampoo. The polymer of this patent application can be applied via a simple aqueous solution in the form of a spray.

These UV-absorbing polymers based on substituted acrylamide backbone exhibit switchable sensitivity towards heat stimulus. The polymer that is soluble in water at ambient temperature becomes insoluble in water at the temperature of human body. It also shows similar sensitivity of becoming insoluble by the presence of salt (inorganic electrolytes in general). The positively charged quaternary ammonium centre helps to adhere to negatively charged hair and skin surface by cationic and anionic charge interaction. The temperature of body (37° C.) renders the film of the applied polymer on skin water-insoluble. Skin, the largest organ, protects the other organs inside the living body. However, the protective mantel of skin needs to be protected from the damaging effect of solar radiation. The damage to skin starts with the reddening and burning of the skin upon exposure and the chronic exposure ultimately leads to skin cancer. The application of this heat and salt sensitivity is very useful for sunscreen preparations that are used by swimmers and surfers at the sea. Both body temperature and salt content of the sea water work favourably to resist the 'washing away' of the applied thin film of 'heat and salt sensitive' UV-absorbing polymers by sea water. The other advantage of these UV-absorbing polymers based on substituted acrylamide is that they can be removed very easily by the water at ambient temperature.

Polymeric UV-absorbers are far safer than the low molecular weight sunscreens with respect to the possibility of exerting toxic effect due to percutaneous absorption (skin penetration) and getting into blood stream (Bos J. and M. Meinardi, *Exp. Dermatol.* 9:165-9 (2002)). These polymers are water-soluble and are not expected to accumulate in lipids of living system and hence expected to be environmentally benign.

Thus, the 'heat and salt sensitive' UV-absorbing macromolecules are perfectly suitable for personal care application because these 1) protect skin and hair from ravages of solar radiation, 2) respond reversibly to the stimuli of both heat and salt (electrolyte), 3) are easy to apply and formulate due to water solubility, 4) are macromolecules and hence very safe in terms of penetration through skin (500 Dalton rule, by J, D Bos and H M H H Meinardi, Expt Dermatology, 165-169, 9, (2000), 5) are eco-friendly since they exhibit no possibility of accumulation in lipids of aquatic animal since they are lipid insoluble, 5) are self-preserving, and 6) show decent antimicrobial activity which is useful for hygiene of skin and scalp.

Occurrence of skin cancer is very high in the world with light colored skin population. In countries like Australia skin cancer is the second biggest killer of human population after coronary heart disease where going to a beach for recreational activity is very common place. (https://www.cnn.com/2018/05/08/health/australia-melanoma-skin-cancer-high-rates intl/index.htm). The revelers and holiday makers keep applying sunscreens to get the adequate protection. However, use of heavy amount of synthetic UV absorbers is dangerous not only to the human (due to systemic effect) but to the environment also. Use of small (non-polymeric) synthetic organic sunscreen is regulated in all countries with a fixed the upper limit for the usage. For example, in the USA, Octyl methoxy cinnamate is allowed only up to 6.5% in the final sunscreen formulation and for Avobenzone, another popular sunscreen molecule, the permissible limit is 3% max. UV-absorbing sunscreening agents are regulated by Food and Drug administration of the Federal Government of the USA. It should be also noted that excessive usage of sunscreens by human population affects the marine life including corals in the sea and states of Florida and Hawaii have restricted use of certain monomeric small UV-absorbers like Octyl methoxy cinnamate and Benzophenone-3 (https://www.nytimes.com/2019/02/07/us/sunscreen-coral-reef-key-west.html; https://news.nationalgeographic.com/2016/05/160502-reef-florida-acidification-fish-miami/, https://link.springer.com/article/10.1007/s00244-015-0227-7).

In the ocean around Palau, it has been estimated that 6,000 to 14,000 tons of sunscreens get washed off people and go into reef areas every year because of the human activity of scuba diving, snorkeling and swimming. The commonly used sunscreen formulations invariably have octyl methoxy cinnamate (OMC) and oxybenzone (Benzophenone-3) since these are relatively cheap monomeric UV absorbers. The formulators have been now creating 'reef-safe' formulations and trying to use other UV absorbers. However, most monomeric, small molecule-UV absorber will have same problems. The only other option is to use UV absorbers that will not get washed off easily so that overall the usage level significantly goes down and that would not penetrate the living cell to exert toxic effects as a result of bioaccumulation. Polymeric UV-absorbers that are substantive and that avoid repeat application can address the issue of polluting the environment, particularly oceans, lakes and rivers.

Hence it is very important to use the sunscreens that would stay on the skin and one doesn't feel the need to apply them again and again and eventually pollute the environment. Also, it is equally important that to have sunscreen molecules to be large enough to resist permeation through the stratum corneum, the skin's upper layer. It is important that the molecules are not lipid-soluble so that the bioaccumulation in fatty/lipids of aquatic animals doesn't occur. The heat and salt sensitive PNIPAM based UV absorbing polymers have all the desired properties listed above. They resist skin permeation since they are too big in size and they are neither water-soluble (at human body temp.) nor are they oil-soluble to bio accumulate in fat tissue of living organisms. Thus, their size and solubility make them useful for sunscreen application for personal care and with respect to ecology as well.

However, these well designed stimuli responsive polymers did not see the light of the day in terms of commercial scale manufacture. This is solely because process of U.S. Pat. No. 7,087,692 is not amenable for scale-up to metric tonne scale. Both polymerization and quaternization processes involve flammable solvents and that too in huge quantity. The yields of desired polymer are too low to be commercial.

The first step of polymerization described in U.S. Pat. No. 7,087,692 involves t-butanol and n-hexane and the second step of quaternization involves isopropanol. The polymer is produced at very low concentration of 10% in t-butanolic solution and to isolate (precipitate) the copolymer from t-butanolic solution after the completion of polymerization one has to use significantly high amount of flammable solvent. (For example, 13 g polymer synthesis uses about 120 mL of t-butanol and 1000 mL of hexane). It should be noted that hydrocarbon solvent like hexane is 'class A' fire hazard. The ratio of copolymer obtained to hexane used is almost 10 to 1000. The solvent precipitation of polymer results a mixture of solvents and hexane needs to be separated from t-butanol for recycling by fractional distillation. Overall the process is not only hazardous but also not eco-efficient. Low yield of desired copolymer is due to 1:100 ratio of product to solvent. It also results in longer batch cycle time and has several chemical engineering unit operations like filtration (filtering precipitated polymer) and fractional distillation (to separate the 'used' solvents). The solvent mix of n-hexane and t-butanol cannot be reused/recycle unless separated.

Objectives of the Invention

It is an objective of the present invention to overcome the drawbacks of the prior art.

It is an objective of the present invention to provide industrially feasible process for manufacture of the UV-absorbing polymers that exhibit lower critical solution temperature (LCST) in water.

It is another objective of the present invention to provide a process for the industrial manufacture of these stimuli responsive polymers using the mosteco-friendly medium of water.

It is yet another objective of this invention to provide a process that would avoid organic solvents, multiple purification steps and engineering unit operations for recovering the solvents and recycling.

It is yet another objective of the present invention to provide an eco-efficient and cost effective process with 100% atom economy.

It is yet another objective to provide an industrial process that does not produce any wastage/effluents.

It is yet another objective to provide UV-absorbing polymers that are substantive to hair and skin surface and stimuli responsive and hence suitable for personal care application.

It is a further objective to provide UV-absorbing polymers or macromolecules that are easy to apply and easy to remove whenever UV protection is not needed without being tacky to hair and skin.

It is yet another objective to provide UV absorbing polymers that are large enough to resist the percutaneous absorption and bioaccumulation in living cells.

SUMMARY OF THE INVENTION

In an aspect of the present invention there is provided a process to produce stimuli responsive UV absorbing water-soluble polymers of Formula I;

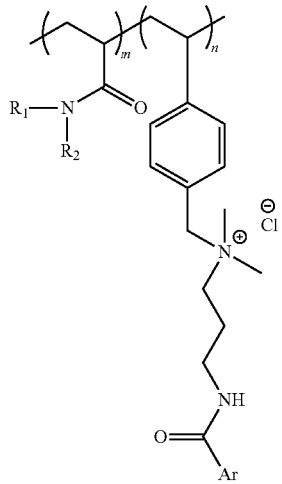

Formula I wherein, ArCO is an UV absorbing moiety selected from 2-cyano-3,3-diphenyl acryloyl and p-methoxy cinnamoyl, $R_1$ is selected from H and $C_1$-$C_3$ alkyl group and $R_2$ is selected from $C_1$-$C_3$ alkyl group, n and m are integers for the moles of monomers and a ratio of m to n is 40:5 to 40:1, and the said process comprises of a) synthesizing of monomers (Formula IV) by quaternization of corresponding tertiary amines (Formula II) with p-vinyl benzyl chloride (Formula III) in aqueous medium; and b) copolymerizing in aqueous medium using water-soluble radical initiators and monomers (Formula IV) of step (a) with N-substituted acrylamides (Formula V) wherein $R_1$ is selected from H and $C_1$-$C_3$ alkyl group and $R_2$ is selected from $C_1$-$C_3$ alkyl group, wherein aqueous solution of compound of Formula V (60-90% of total by weight) and water-soluble radical initiator are gradually added simultaneously to a stirred and preheated aqueous solution of compound of Formula IV and compound of Formula V (10-40% of the total) under nitrogen over a period of time.

BRIEF DESCRIPTION OF THE ACCOMPANYING DRAWINGS

DETAILED DESCRIPTION OF THE INVENTION

Figure 1:
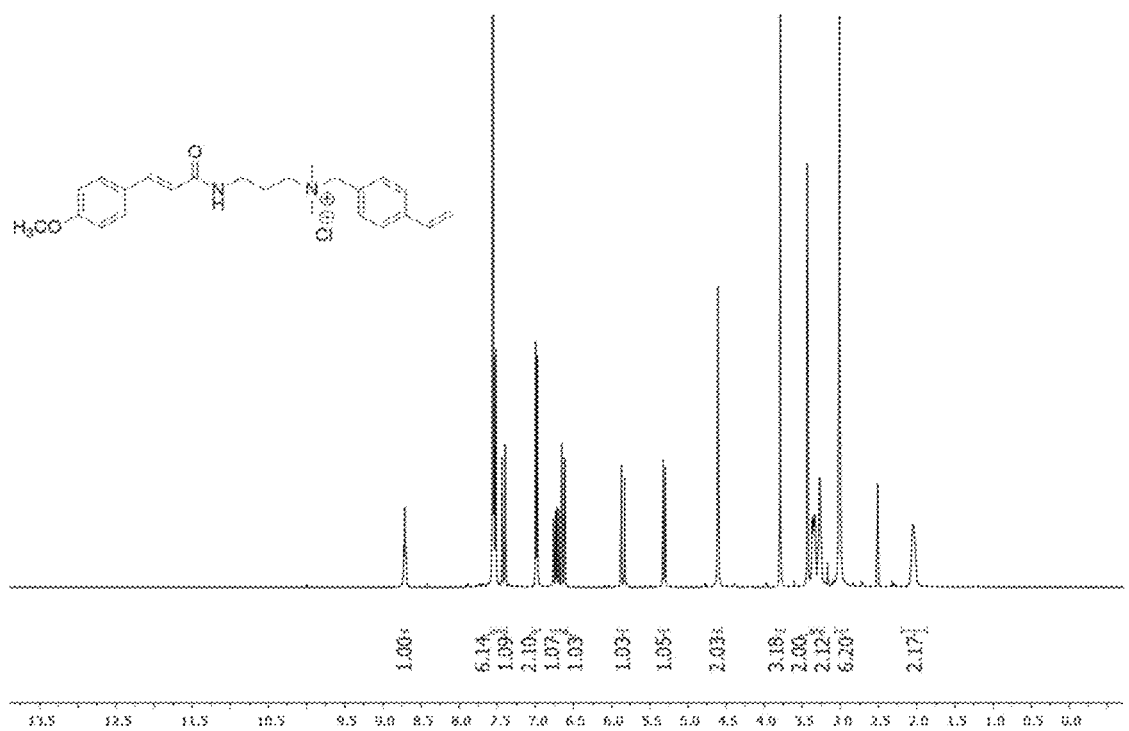
FIG. 1 illustrates Proton magnetic resonance spectrum of p-methoxy cinnamido propyl, p-vinyl benzyl dimethyl ammonium chloride (Formula IVa).

The present invention describes an aqueous process for the synthesis of cationic UV-absorbing monomers and their copolymerization with substituted acrylamides in water to yield the substantive and stimuli responsive copolymers depicted by Formula I;

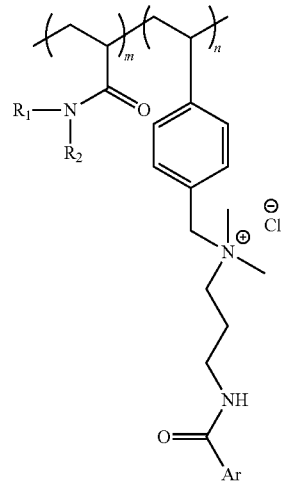

Formula I wherein ArCO is an UV-absorbing moiety selected from 2-cyano-3,3-diphenyl acryloyl and p-methoxy cinnamoyl, $R_1$ is selected from H, $C_1$-$C_3$ alkyl group and $R_2$ is selected from $C_1$-$C_3$ alkyl group, m and are integers and and a ratio of m to n is 40:5 to 40:1.

The following description with reference to the accompanying drawings is provided to assist in a comprehensive understanding of exemplary embodiments of the invention. It includes various specific details to assist in that understanding but these are to be regarded as merely exemplary. Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof. Also, expressions such as "at least one of," when preceding a list of elements, modify the entire list of elements and do not modify the individual elements of the list.

Temperature responsive polymers are reported for drug delivery and the most popular ones are based on substituted acrylamides (Dirk Schmaljohann, "Thermo and pH responsive polymers in drug delivery", *Advanced Drug Delivery Reviews*, Vol 58, 1655-1670, 2006). In addition to drug delivery, the thermo-responsiveness of poly N-substituted acrylamides has been proposed for protecting skin from solar damage (personal care). As described in the background (U.S. Pat. No. 7,087,692) section of this application the thermo-responsiveness is derived from the property of 'inverse temperature dependent solubility' of poly-N-substituted acrylamides for personal care (sun protection) application, however, it remained unexploited for last two decades simply because the synthesis reported in the prior art is unsuitable (not sustainable) for commercial manufacture due to heavy use of flammable solvents that posed fire as well health hazard (U.S. Pat. No. 7,087,692). In addition, the reported synthesis had been cost-prohibitive simply because of the cost of solvents and also because of the volatile nature of the solvents that results in some unavoidable loss while handling solvents. Since two solvents (tertiary butanol and n-hexane) deployed in polymerization step of the prior art need to be separated for recycling them, one has to incur the cost of the separation/fractionation unit operation. Volatile nature of the solvents also has impact on the environment which is something inevitable.

The present invention avoids use of organic flammable solvents in polymer synthesis that are used in the prior art U.S. Pat. No. 7,087,692 (2006). In addition, the present invention uses the approach of copolymerizing functionalized UV-absorbing monomers that too are synthesized in water medium. Thus, the method of making stimuli responsive UV-absorbing polymers comprises of two steps that are performed in water obviating the use of organic solvents. The polymer synthesis of this patent application involves two steps as described below.

Step 1: Aqueous Synthesis of Monomers of Formula IV, Namely, p-Methoxy Cinnamido Propyl p-Vinyl Benzyl Dimethyl Ammonium Chloride (Formula IVa) and 2-Cyano-3,3-Diphenyl Acrylamido Propyl p-Vinyl Benzyl Dimethyl Ammonium Chloride (Formula IVb).

The quaternization of p-methoxy cinnamido propyl dimethyl amine and/or 2-cyano-N-(3-(dimethylamino)propyl)-3,3-diphenylacrylamide (Formula II) with p-vinyl benzyl chloride (Formula III) is carried out in aqueous media.

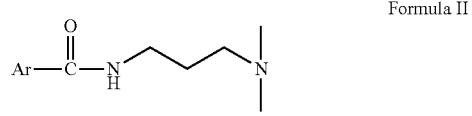

Formula II

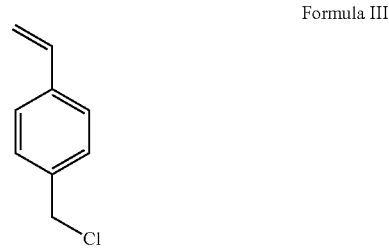

Formula III

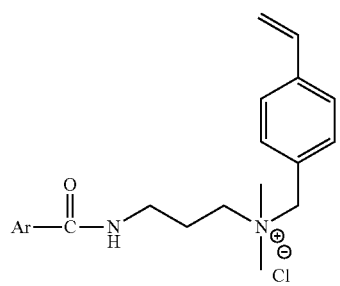

Formula IV

Step 2: Aqueous Synthesis of the Copolymer of Formula I:

Quaternary compound of Formula IV and N-substituted acrylamides (Formula V) are copolymerized in an aqueous medium to give UV-absorbing stimuli responsive polymers of Formula I.

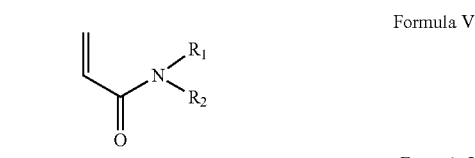

Formula V

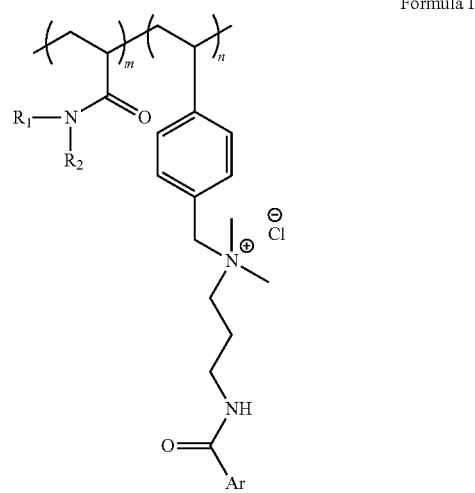

Formula I

The synthesis of copolymers represented by Formula I of the present invention is carried out by a two-step procedure, namely, a) aqueous synthesis of vinylic UV-absorbers with quaternary centres built-in (compounds of Formula IV) and b) copolymerization of compounds of Formula IV with substituted acrylamides of Formula V that exhibit 'inverse temperature dependent solubility' in water (Examples I, II, III and IV).

Scheme 2

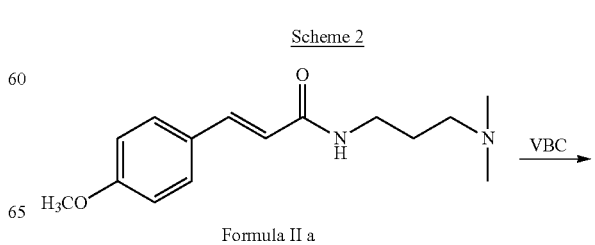

Formula II a

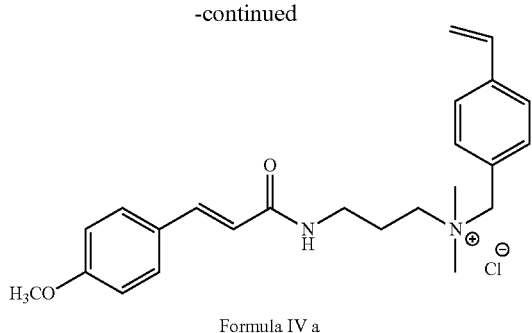

Formula IV a

The first step of the process of this patent application is facile and quantitative quaternization reaction in water medium wherein water-insoluble vinyl benzyl chloride is reacted with another water-insoluble UV-absorbing compound (Formula II) with terminal tertiary amino group. The surprising and unexpected finding is the second step of facile copolymerization of quaternized UV-absorbing monomers (Formula IV) with acrylamide derivatives in water medium using water-soluble radical initiators with decomposition temperatures significantly above the lower critical solution temperatures (LCSTs) of the resultant copolymers in water. The copolymers of Formula I exhibit 'inverse temperature dependent solubility' in water.

The first step of the process involves aqueous synthesis of monomers of Formula IV, namely, p-methoxy cinnamido propyl p-vinyl benzyl dimethyl ammonium chloride (Formula IVa) and 2-cyano-3,3-diphenyl acrylamido propyl p-vinyl benzyl dimethyl ammonium chloride (Formula IVb).

In one embodiment, the synthesis of p-methoxy cinnamido propyl p-vinyl benzyl dimethyl ammonium chloride (Formula IVa) involves p-methoxy cinnamidopropyl dimethyl amine (Formula IIa) procured from Galaxy Surfactants, India (Scheme 2). This UV-absorbing tertiary amine (Formula IIa) is used in making of commercial product which is a water-soluble sunscreen, Galaxy SunBeat (3-(N-p-methoxy cinnamidopropyl)-N,N-dimethyl ammonium) 2-hydroxypropane-1-sulphonate, CAS 500731-87-3).

p-Methoxy cinnamidopropyl dimethyl amine has highly conjugated system resulting into very high UV-absorbing property (molar extinction coefficient of 24,000 at 290 nm). This strong UV absorbing compound (Formula IIa) is quaternized with p-vinyl benzyl chloride (Formula III) in aqueous medium at 80° C. and the quaternization reaction is monitored by estimating the quantitative generation of chloride ion by Mohr's method (Example I, Scheme 2). The solids content of the reaction mass of this step is kept at around 30% by weight Proton magnetic resonance spectrum of the dried material reveals the chemical shift of the trans-double bonded protons at δ 6.61-6.65 and δ 7.39-7.43 with J value of 16 Hz as shown in FIG. 1. $E^{1\%}_{cm}$ 463 at $\lambda_{max}$ 310 nm (Step (a) of Example I).

The vinylic quaternized UV-absorbing monomer (Formula IVa, scheme 2) is then copolymerized with N-isopropyl acrylamide (Formula V) in the molar ratio of 1:40 in the aqueous medium using water-soluble radical initiators at 60° C. to 80° C. to afford the UV-absorbing copolymer (Formula Ia, scheme 3). The solids content of aqueous copolymerization is kept around 20%.

The inventors of the present application surprisingly found that the UV-absorbing monomer (Formula $IV_a$) with substituted acrylamide gets quantitatively copolymerized in water at temperatures that are significantly higher than the LCST of resultant copolymer. In a typical reaction, aqueous solution of radical initiator and aqueous solution of substituted acrylamide (60-90% by weight of the total) are added simultaneously to a stirred and heated aqueous solution of UV-absorbing monomer of Formula IV under nitrogen atmosphere and substituted acrylamide of Formula V (10-40% by weight of the total) at 60-80° C. The water-soluble radical initiators employed ranging from 1.0 to 10% on the basis of the weight of solids content of reaction mass due to monomers in the step b of Examples I, II, III and IV. In one embodiment, ammonium persulphate is the initiator in the step b of Examples I, II, III and IV.

It is very obvious to the person skilled in the art that other inorganic 'per' salts can be used, for example sodium persulphate or potassium persulphate. Simple aqueous solution of hydrogen peroxide can also be used as radical initiator. In addition to 'per' compounds, other suitable water-soluble 'azo' radical initiators can be used as well. 2,2'-Azobis(2-methyl propionamidine)dihydrochloride) or 4, 4'-Azobis(4-cyanovaleric acid) are the examples of such water-soluble initiators that can be used for effecting copolymerization. A variety of water-soluble radical initiators the temperatures can be deployed with small variations in the temperature at which reactions are conducted based their decomposition points.

Scheme 3

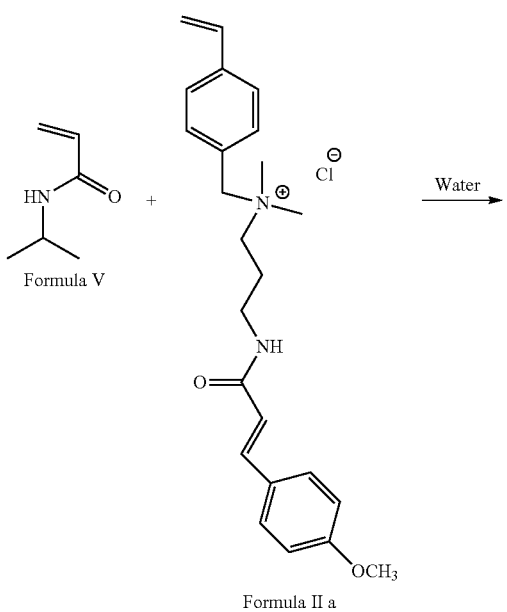

Formula V

Formula II a

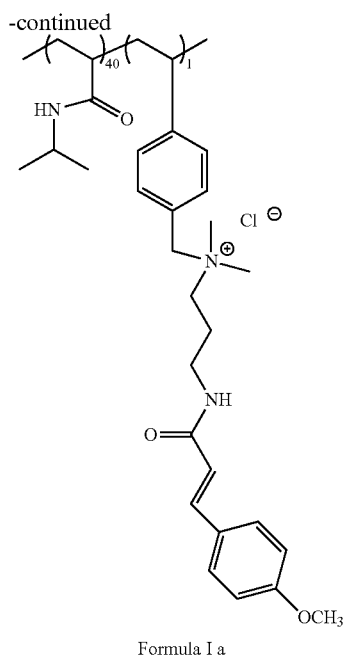

Formula I a

Figure 2:
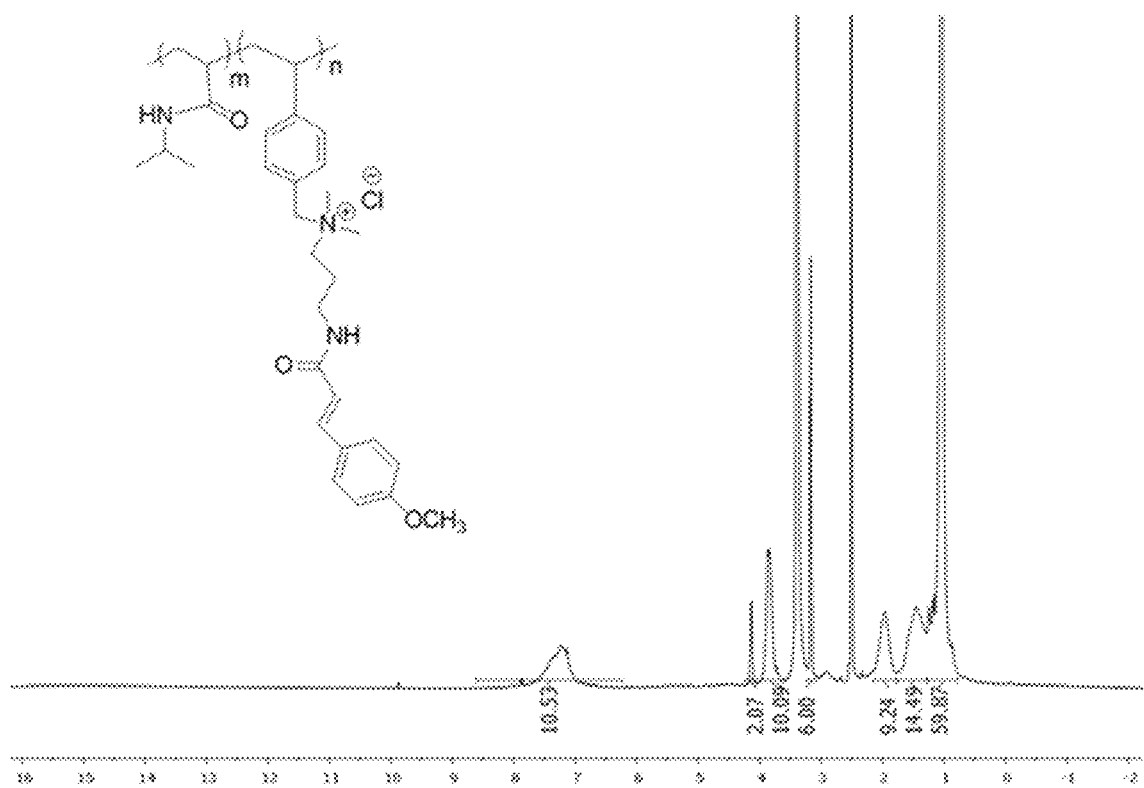
FIG. 2 illustrates Proton magnetic resonance spectrum of UV-absorbing copolymer (Formula Ia).

Both monomers e.g. compounds of Formula IV and N-substituted acrylamides are soluble in water, however, the copolymer formed is insoluble in aqueous medium at the temperature at which the reactions are run (Step (b) of Example I). The copolymer precipitates from the reaction mixture as it gets formed. Using Mark-Houwink-Sakurada equation based on intrinsic viscosity of this copolymer (Example I, Formula I) the weight average molecular weight is found to be $6.50 \times 10^4$ grams/mole. This surprising result of successful copolymerization, is at least, in part, attributed to the surfactant properties of quaternary vinylic monomers of Formula IV. These cationic monomeric compounds of Formula IV do show surface activity (reduce surface tension of water from 72 mN/m to around 40 mN/m) and thereby keep the polymer chains formed solubilized in water by micellization and allowing them to grow of at temperature of reaction which is way above the LCST before crashing out aqueous medium. Thus, when the surface active vinylic quaternary monomer (Formula IV) gets completely copolymerized with substituted acrylamides (Formula V) and no longer available for micellization then the copolymer (Formula I) separates from aqueous solution at reaction temperature which is higher than the LCST of the copolymer. The precipitated copolymer is separated after decanting the hot water of reaction mass and the coagulated polymer is re-dissolved in fresh water to yield a clear solution at room temperature with the desired concentration. The decanted hot water from the reaction mass does not show any presence of unpolymerized UV-absorbing monomer of Formula IV by UV-spectroscopic examination. Nuclear magnetic resonance spectroscopy of the dry copolymer sample reveals the complete disappearance of vinylic protons indicating quantitative copolymerization as evident from FIG. 2. $E^{1\%}{}_{cm}$ is 29 at $\lambda_{max}$ 310 nm. The thermosensitivity (LCST) of the resulting copolymers varies with the change in the ratio (m:n) of monomers. Higher participation of hydrophilic UV absorbing monomer (Formula IV) in the copolymer (Formula I) raises the lower critical solution temperature (LCST). Example IV describes the synthesis of copolymer wherein the molar ratio of N-isopropyl acrylamide to vinylic UV-absorbing monomer of Formula IV is 40:4 (m:n:: 40:4). Increased percentage of UV-absorbing monomer in the copolymer results in higher UV-absorption power ($E^{1\%}{}_{cm}$ was found to be 82.0 at $\lambda_{max}$ 310 nm) and increase the Lower Critical solution temperature (34 to 36° C.) but crossing the body temperature of 37° C.

Figure 3:
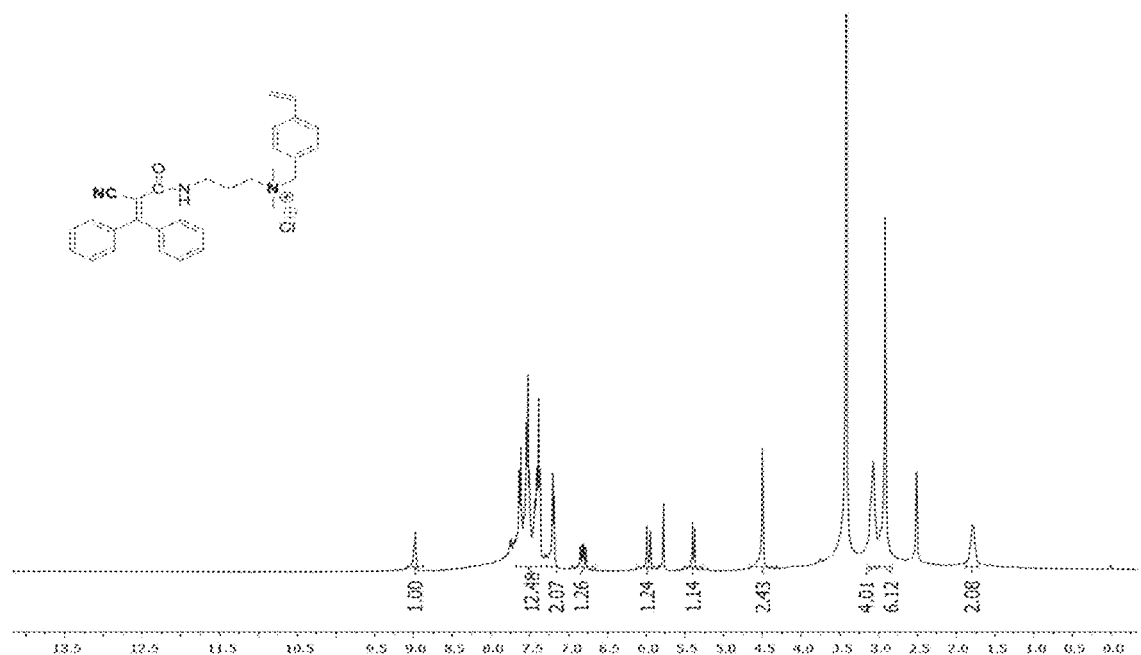
FIG. 3 illustrates proton NMR of 2-cyano-3,3-diphenyl acrylamido propyl p-vinyl benzyl dimethyl ammonium chloride (Formula IVb).

Similarly, 2-cyano-3,3-diphenyl acrylamidopropyl p-vinyl benzyl dimethyl ammonium chloride (Formula IVb) is copolymerized with substituted acrylamide as shown in the scheme 4. 2-Cyano-3,3-diphenylacrylamido N',N'-dimethyl propyl diamine (Formula IIb) in turn is synthesized from corresponding 2-cyano-3,3-diphenyl acrylic acid as given in Example II. Quaternizing the tertiary amine (Formula IIb) with p-vinyl benzyl chloride (Formula III) affords surface active quaternary UV-absorbing 2-cyano, 3,3-diphenyl acrylamido propyl p-vinyl benzyl dimethyl ammonium chloride (Formula IVb; scheme 4). Completion of quaternization is ascertained by the estimation of liberated chloride ion in the reaction mass. The quaternized UV-absorber ($E^{1\%}{}_{cm}$ at 178 at $\lambda_{max}$ 305 nm) showed surface activity (1% aqueous solution 40.2 mN/m). IR of dry sample shows nitrile stretch at 2212 $cm^{-1}$ and proton NMR (FIG. 3) shows the coupling of vinylic protons. (Example II).

Copolymerization of 2-cyano-3,3-diphenylacrylamido propyl p-vinyl benzyl dimethyl ammonium chloride (Formula IVb) with substituted acrylamide (N,N-isopropyl acrylamide) (Formula V) in water is performed as described in Example II, scheme 5. Spectroscopic examination of the dry sample copolymer (Formula Ib) indicates the absence of UV-absorbing monomer of Formula IVb in the product.

The copolymer of Formula Ib showed the LCST of 30-32° C. The intrinsic viscosity is determined by Ubbelohde viscometer. The weight average molecular weight of copolymer ($k=9.59 \times 10^{-3}$ and $a=0.65$) is found to be $6.50 \times 10^4$ grams/mole. $E^{1\%}{}_{cm}$ of the copolymer is 29 at $\lambda_{max}$ 305 nm.

Scheme 4

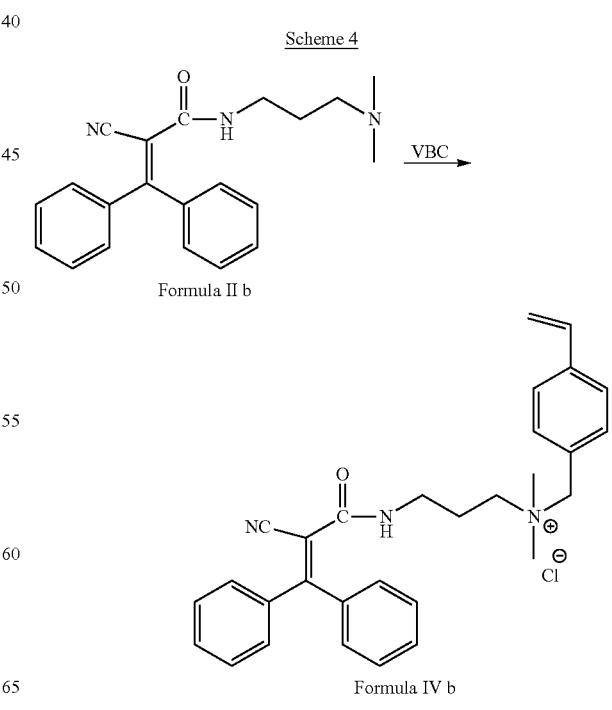

Formula II b

Formula IV b

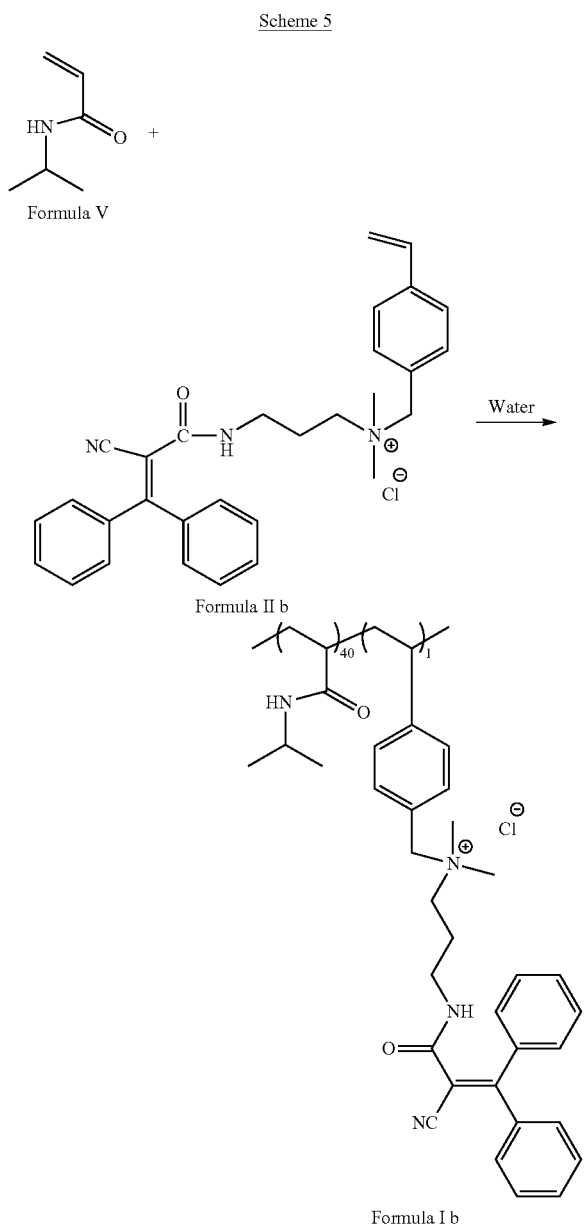

Scheme 5

Formula V

Formula II b

Formula I b

The Examples I and II demonstrate the copolymers of Formula I with N-isopropyl acrylamide with UV-absorbing monomer in the ratio of 40:1. Analogous chemistry is performed in Example III with N,N-diethylacrylamide and p-methoxy cinnamido propyl p-vinyl benzyl dimethyl ammonium chloride. As mentioned above, Example IV depicts copolymer synthesis with higher participation of UV-absorbing monomer in the molar ratio with respect to N-substituted acrylamide (m=40 and n=4). The copolymers of Formula I can be used in personal care formulation as demonstrated by Examples V and VI illustrate suitability of UV-absorbing polymer (Example II) in personal care formulations, namely, a cream and a spray formulation.

UV absorbers for personal care are generally divided into two categories based on their light absorption properties, UV B (290-320 nm) and UV-A (320-400 nm). Personal care formulations for skin care are supposed to provide adequate protection against the entire UV range covering both UV-A and UV-B zones since both ranges have been reported to be quite harmful. It is not only the general awareness of consumers desiring UV-A protection but the regulatory bodies have made it compulsory by issuing guidelines to balance the UV-B and UV-A protection in the personal care products that are sold as sunscreens. COLIPA (The European Cosmetic and Perfumery Association, (2006)) demands that UV-A protection factor (PFA) should be at least one third of SPF (UV-B protection). What it means is that the ratio of labelled SPF to PFA should be no greater than 3 and the critical wavelength is also defined at λ370 nm in UV-A region. Thus, it is now mandatory to have both UV-A and UV-B protection in sunscreen formulations and it is mandatory to indicate UV-A protection factor alongside SPF number which corresponds to UV-B protection.

Octyl methoxy cinnamate (CAS number 5466-77-3) is a UV B absorber with λmax of 302 whereas Avobenzone (CAS number 70356-09) is an UV-A absorber with λmax of 360 nm. Both UV absorbers are work-horses of sunscreen formulations. Unfortunately, both UV absorbing molecules by themselves are not stable and also these destabilize each other when present together in a formulation. (D. Dondi, A. Albinia, N. Serpone., Interactions between different solar UV-B/UV-A filters contained in commercial sunscreens and consequent loss of UV protection, *Photochem. Photobio. Sci.*, 2006, 5, 835-843). Fortuitously, it has been discovered that Octocrylene (CAS number 6197-30) quenches the excited states of both OMC (octyl methoxy cinnamate) and Avobenzone by singlet-singlet and triplet-triplet quenching mechanism and thereby preventing the undesired photo-degradation or photochemical reactions leading to destruction of UV absorbing chromophore. This quenching mechanism is possible due to unique structure of chromophore i.e. 2-cyano-3,3-diphenyl acryloyl moiety of Octocrylene (Bonda et al. U.S. Pat. Nos. 7,597,825, 7,915,330).

In view of this prior art, the thermosensitive copolymer of Example II, scheme 4, with the chromophore of 2-cyano-3,3-diphenyl acryloyl moiety, is useful in arresting the photo-degradation of OMC and Avobenzone. In addition, it absorbs in the UV B region with max 305 nm. Example VII is a cream formulation with OMC and Avobenzone is exposed for 200 h using UV light from a UV lamp. During this period OMC degraded from 6% to 2% and Avobenzone degraded from original 2.0% to 0.1%. Similar cream formulation (Example VIII) is prepared using 10% copolymer of Example II. Upon similar exposure of UV and under identical set of conditions the photo-degradation of both OMC and Avobenzone is significantly arrested as shown in the below Table 1.

TABLE 1

Photo-degradation studies OMC, Avobenzone and copolymer of Example II

| | Cream Example VII | | | Cream of Example VIII | | |
|---|---|---|---|---|---|---|
| Component | Zero h | Un-exposed | UV exposure 200 h | Zero h | Un-exposed | UV exposure 200 h |
| OMC | 6.0% | 6.0% | 2.0% | 6.0% | 6.0% | 4.5% |
| Avobenzone | 2.0% | 2.0% | 0.1% | 2.0% | 2.0% | 1.5% |
| Copolymer of Example II | | | | 10% | | |

Advantages of the Invention

1) The stimuli-responsive UV-absorbing polymers have been (U.S. Pat. No. 7,087,692 (2006)) reported to be useful for personal care applications because of their ability to bind to the skin and hair and due to their reversible water-solubility as a response to heat or salt. However, the reported synthesis has not been amenable for the commercial manufacture. The present invention provides an industrially feasible route of manufacture of these thermosensitive and salt-sensitive UV-absorbing polymers that meet the principles of 'green' chemistry. The synthesis employs commercially available olefinic monomers. The conversions are quantitative giving 100% atom economy and hence at no stage any purification is needed. The synthesis does involve catalysis and thereby a complete control over the rate of the reaction. There is no waste generation and hence no waste disposal. Shorter batch cycle time and lesser chemical engineering unit operations make the new process industrially and economically viable.

2) The biggest advantage for the process of manufacture of UV-absorbing, stimuli responsive, cationic polymers comes from carrying both steps in aqueous medium. This also makes the process cost-effective as well as safe since it avoids flammable solvents of the prior art. Water based synthesis of the present invention removes not only the fire hazards but it also makes the process safe to the working personnel.

3) The UV-absorbing polymers are large enough (molecular weight above 500 grams/mole, typically 5,000 to 200,000 grams/mole) to resist the percutaneous absorption. The high water-solubility of the copolymers precludes the possibility of bioaccumulation in lipid tissue of aquatic animals.

4) The UV-absorbing copolymers of this patent application are easy to apply and easy to remove.

5) The thermosensitive copolymer of this patent application (Example II below and Table I above) is effective in photostabilizing some of the current work-horse sunscreen molecules like octyl methoxy cinnamate or Avobenzone.

EXAMPLES

The invention will now be illustrated with the help of examples. Example I to IV illustrate the process of manufacture of copolymers of Formula I and Examples V, VI and VIII illustrate for the personal care compositions using polymers of Formula I. These examples are by way of illustration only and in no way restrict the scope of invention. Many changes and modifications can be made within the scope of the present invention without departing from the spirit thereof and the invention includes all such modifications.

p-Methoxy cinnamido propyl dimethyl amine was obtained from Galaxy Surfactants Ltd., Mumbai. Vinyl benzyl chloride was purchased from Seimi Chemical Co., Ltd. Japan. N, N-Diethyl acrylamide was obtained from Sigma Aldrich, India. N-isoproyl acrylamide was synthesized as per the literature procedure (*Polym. J.*, Vol. 25, No. 6, pp. 561-567). Surface tension was measured on Kruss tensiometer by Wilhelmy plate method. Intrinsic viscosity was measured by Ubbelohde viscometer. NMR spectroscopy was done on 400 MHz Bruker machine. Infrared spectra were recorded on FTIR from Perkin Elmer (Spectrum 100). UV Varian's, Cary 50 absorption spectrophotometer was used for UV absorption data.

Example I

The process for preparation of copolymer of Formula Ia; wherein ArCO=p-methoxy cinnamoyl, $R_1$=H, $R_2$= isopropyl; mole ratio, m:n::40:1

This copolymer was synthesized by the following two steps.

(a) Preparation of p-Methoxy Cinnamido Propyl p-Vinyl Benzyl Dimethyl Ammonium Chloride A mixture of vinyl benzyl chloride (19.08 g, 125 mmol), p-methoxy cinnamido propyl dimethyl amine (32.77 g, 125 mmol) and water (118 g) was stirred under nitrogen at 75-80° C. for 8 hours. The progress of the reaction was conveniently monitored by measuring the liberated chloride ion. The quaternized product was obtained as clear, colorless solution with solids contents of 30% and chloride ion content of 4.22%. Yield 172.0 g. $E^{1\%}_{cm}$ 568 at m 310 nm. A small dried sample was used for recoding IR and NMR analysis. IR: 1662 cm$^{-1}$, 2966 cm$^{-1}$, 3260 cm$^{-1}$. Surface tension of 1% aqueous solution is 42.6 mN/m.

$^1$H NMR (400 MHz, DMSO-d$_6$): δ 2.06 (m, 2H), 3.01 (s, 6H), 3.29 (m, 2H), 3.37 (m, 3H) 4.60 (s, 2H), 5.32 (d, 1H. J=12 Hz), 5.87 (d, 1H, J=16 Hz), 6.65 (d, 1H, J=16 Hz), 6.76 (m, 1H), 6.99 (d, 2H, J=8 Hz), 7.43 (d, 1H, J=16 Hz), 7.55 (m, 6H), δ 8.72 (t, 1H).

$^{13}$C NMR (100 MHz, DMSO-d$_6$): δ 23.28, 36.14, 49.83, 61.72, 62.98, 66.10, 114.86, 116.58, 120.04, 126.34, 126.94, 127.86, 129.58, 133.73, 136.22, 138.92, 139.24, 160.75, 166.10.

(b) Copolymerization of N-Isopropyl Acrylamide and p-Methoxy Cinnamido Propyl p-Vinyl Benzyl Dimethyl Ammonium Chloride (m:n::40:1)

A mixture of p-methoxy cinnamido propyl p-vinyl benzyl dimethyl ammonium chloride, 30% solution from step (a) (13.52 g, 9.7 mmol), N-isopropyl acrylamide (9.05 g, 79.97 mmol) (20% of total) and water (105 mL) was stirred at 70° C. under nitrogen blanket.

To the above preheated and stirred solution. N-isopropyl acrylamide (36.2 g, 320 mmol) (80% of total) in water (65 mL) and ammonium persulphate (3.650 g, 16.0 mmol) in water (40 mL) were added gradually (N-isopropyl acrylamide over 5 h and ammonium persulphate over 6 h) and continued to stir at 70° C. for additional 2 h after the persulphate addition was complete.

The precipitated copolymer was separated from the reaction mixture by decantation and it was redissolved in distilled water to make 20% clear and pale yellow colored solution that had the viscosity of 280 cps at 25° C.

It showed the LCST of 30-32° C. Yield 250.0 g (89.0%). The intrinsic viscosity was determined by Ubbelohde viscometer. The weight average molecular weight of copolymer (k=9.59×10$^{-3}$ and a=0.65) was found to be 6.50×10$^4$ grams/mole. $E^{1\%}_{cm}$ was found to be 40 at $\lambda_{max}$ 310 nm.

IR and NMR analysis of the dried sample is as follows: IR: 1626 cm$^{-1}$, 2975 cm$^{-1}$, 3282 cm$^{-1}$. $^1$H NMR (400 MHz, DMSO-d6): δ broad signal at 1.04, 1.46, 1.96, 3.17, 3.82, 4.14, 7.34.

Example II

The Process for Preparation of Copolymer of Formula Ib; Wherein ArCO=2-Cyano-3,3-Diphenyl Acryloyl, $R_1$=H, $R_2$=Isopropyl; Mole Ratio, m:n::40:1

The UV-absorbing 2-cyano-3,3-diphenyl acrylamido N'N'-dimethyl propyl diamine is synthesized by the following procedure.

Synthesis of α-Cyano, β,β-Diphenyl Acrylic Acid

A mixture of methyl α-cyano-β,β-diphenyl acrylate (263 g, 1.0 mol) and sodium hydroxide (44 g, 1.1 mol) in aqueous methanol (1:1, 1200 mL) was refluxed for four hrs. The reaction mixture was then cooled and acidified with aqueous hydrochloric acid (pH of 1.0) to precipitate the α-cyano, β,β-diphenyl acrylic acid as off-white solid. It was filtered and washed with water to remove the mineral acidity. Drying yielded 240 g (96%) of white powder. Acid value: 225, mp: 208° C.

FTIR: 1683 cm$^{-1}$, CO of carboxyl group, 2221 cm$^{-1}$ nitrile group, —OH of carboxyl broad peak ranging from 3200 to 3000 cm$^{-1}$. $^1$H NMR (400 MHz, DMSO-d$_6$): δ 7.18 to 7.55 all aromatic protons, 13.10 (broad singlet, 1H). $^{13}$C NMR (100 MHz, DMSO-d$_6$): δ 105, 49, 117.20, 128.12, 128.55, 129.03, 129.57, 130.03, 130.89, 138.40, 138.68, 163.26, 167.01.

(a) Synthesis of α-cyano-β,β-diphenyl Acrylic Acid

To a stirred mixture of Benzophenone (100 g, 0.54 mol), cyanoacetic acid, 850 g (1.0 mol) in acetic acid 33 g (0.54 mol) and toluene 800 mL was stirred under reflux and under nitrogen using Dean and Stark apparatus was added ammonium acetate (88 g, 1.1 mol) in six installments of 2 hrs. After this the reaction was continued for additional 6 h. The product, α-cyano-β,β-diphenyl acrylic acid separated as white solid (102 g, 74%). It was further crystallized in methanol to get 90 g of α-cyano-β,β-diphenyl acrylic acid. m. p. 208° C.

FTIR: using attenuated total reflectance technique on a solid sample 1683 cm$^{-1}$, CO of carboxyl group, 2221 cm$^{-1}$ nitrile group, —OH of carboxyl broad peak ranging from 3200 to 3000 cm$^{-1}$. $^1$H NMR (400 MHz, DMSO-d$_6$): δ 7.18 to 7.55 all aromatic protons, 13.10 (broad singlet, 1H). $^{13}$C NMR (100 MHz, DMSO-d$_6$): δ 105, 49, 117.20, 128.12, 128.55, 129.03, 129.57, 130.03, 130.89, 138.40, 138.68, 163.26, 167.01.

(b) Preparation of 2-cyano, 3, 3-diphenyl acrylamido N', N'-dimethyl Propyl Diamine To a stirred solution of 2-cyano-3,3-diphenyl acrylic acid (28.43 g, 114.2 mmol) dichloromethane (250 mL) and thionyl chloride (14.30 g, 120.12 mmol) was added slowly under nitrogen medium at ambient temperature. Above reaction mixture was added to N,N-dimethyl aminopropyl amine (11.6 g, 114.2 mmol) in dichloromethane (100 mL) for about 1 h. The stirring was continued for additional four hours at ambient temperature. At this stage water was added and the reaction mixture was cooled to 10-15° C. 2-cyano-3,3-diphenyl acrylamido N',N'-dimethyl propyl amine hydrochloride containing aqueous layer was separated and traces of dichloromethane in aqueous layer was removed under vacuum. The hydrochloride salt solution was basified using sodium hydroxide (45% solution) to the pH of 12. The product, 2-cyano-3,3-diphenyl acrylamido N',N'-dimethyl propyl diamine precipitated as white solid. It was filtered, washed with water and dried under vacuum. A small sample was dried under vacuum for recoding IR and NMR.

IR: 1652 cm$^{-1}$, CO of carboxyl group, 2203 cm$^{-1}$ nitrile group, OH of carboxyl broad peak 3171 cm$^{-1}$ $^1$H NMR (400 MHz, DMSO-d$_6$): δ 1.30 (m, 2H), 1.90 (t, 2H), 2.00 (s, 6H) 3.01 (q, 2H), 7.20 (d, 2H), 7.44 (m, 5H), 7.50 (m, 3H) 8.53 (t, 1H). $^{13}$C NMR (100 MHz, DMSO-d$_6$): δ 26.05, 37.24, 45.02, 56.17, 108.53, 117.22, 128.24, 128.58, 129.31, 129.99, 130.25, 137.65, 138.32, 160.05, 161.78.

This copolymer was synthesized by the following two steps.

(a) Preparation of 2-cyano-3,3-diphenyl Acrylamido Propyl p-Vinyl Benzyl Dimethyl Ammonium Chloride A mixture of vinyl benzyl chloride (7.85 g, 51.5 mmol) 2-cyano-N-(3-(dimethylamino)propyl)-3,3-diphenylacrylamide (17.15 g, 51.5 mmol) from step (b) and water (60 mL) was stirred under nitrogen atmosphere at 75-80° C. for 8 hours. Progress of the reaction was conveniently monitored by measuring the liberated chloride ion content. The quaternized product was obtained as clear colorless solution with solids contents of 30% and chloride ion content of 3.49%. Yield 85.0 g. $E^{1\%}_{cm}$ 496 at $\lambda_{max}$ 305 nm. A small sample was dried under vacuum and used for recoding IR and NMR analysis.

IR: 1651 cm$^{-1}$, 2212 cm$^{-1}$, 3030 cm$^{-1}$, 3370 cm$^{-1}$ Surface tension of 1% aqueous solution is 40.2 mN/m. $^1$H NMR (400 MHz, DMSO-d$_6$) δ 1.78 (s, 2H), 2.91 (s, 6H), 3.07 (m, 4H), 4.49 (s, 2H), 5.40 (d, 1H, J=12 Hz), 5.98 (d, 1H, J=16 Hz), 6.84 (m, 1H), 7.20 (d, 2H, J=8 Hz), S 7.36-7.63 (m, 12H), S 8.99 (t, 1H). $^{13}$C NMR (100 MHz, DMSO-d$_6$): δ 22.14, 36.87, 49.47, 61.50, 66.51, 108.64, 116.67, 117.63, 126.98, 127.81, 128.74, 129.06, 129.75, 129.84, 130.47, 130.81, 133.79, 136.30, 138.24, 138.80, 139.32, 161.31, 162.71.

(b) Copolymerization of N-Isopropyl Acrylamide and 2-Cyano-3,3-Diphenyl Acrylamido Propyl p-Vinyl Benzyl Dimethyl Ammonium Chloride (m:n:: 40:1)

A mixture of 2-cyano-3,3-diphenyl acrylamido propyl p-vinyl benzyl dimethyl ammonium chloride, 30% aqueous solution from step (a) (8.14 g, 5.02 mmol)N-isopropyl acrylamide (4.56 g, 40.29 mmol) (20% of total) and 136 g of water was stirred at 70° C. under nitrogen blanket.

To the above preheated and stirred solution, N-isopropyl acrylamide (18.24 g, 161.18 mmol) (80% of total) in water (150 mL) and ammonium persulphate (1.82 g, 8.0 mmol) in water (50 g) were added gradually (N-isopropyl acrylamide over 5 h and ammonium persulphate over 6 h) and continued to stir at 70° C. for additional 2 h after the persulphate addition was complete.

The precipitated copolymer was separated from the reaction mixture by decantation and it was redissolved in distilled water to make 20% clear and pale yellow colored solution that had the viscosity of 180 cps at 25° C.

It showed the LCST of 32-34° C. Yield 125.0 g. The intrinsic viscosity was determined by Ubbelohde viscometer. The weight average molecular weight of copolymer (k=9.59×10$^{-3}$ and a=0.65) was found to be 6.98×10$^4$ grams/mole. $E^{1\%}_{cm}$ was found to be 37 at $\lambda_{max}$ 310 nm.

A small sample was dried under vacuum and used for recoding IR and NMR analysis.

IR: 1630 cm$^{-1}$, 2218 cm$^{-1}$, 2974 cm$^{-1}$, 3375 cm$^{-1}$. $^1$H NMR (400 MHz, DMSO-d$_6$): δ broad signal at 1.03, 1.44, 1.95, 3.23, 3.84, 4.32, 4.64, 5.40, 7.39, and 7.78.

Example III

The Process for Preparation of Copolymer of Formula I; Wherein ArCO=p-Methoxy Cinnamoyl, R$_1$=Ethyl, R$_2$=Ethyl; Mole Ratio, m:n::40:1

(a) Preparation of p-Methoxy Cinnamido Propyl p-Vinyl Benzyl Dimethyl Ammonium Chloride This was done as per the procedure described in Example I.

(b) Copolymerization of N, N-Diethyl Acrylamide and p-Methoxy Cinnamido Propyl, p-Vinyl Benzyl Dimethyl Ammonium Chloride (m:n:: 40:1)

A mixture of p-methoxy cinnamido propyl p-vinyl benzyl dimethyl ammonium chloride, 30% solution from step (a) (20.0 g, 14.49 mmol) N,N-diethylacrylamide (14.74 g, 115.89 mmol) (20% of total) and water (80 mL) was stirred at 70° C. under nitrogen blanket.

To the above preheated and stirred solution. N,N-diethylacrylamide (58.98 g, 464.0 mmol) (80% of total) in water (70 mL) and ammonium persulphate (4.58 g, 20.07 mmol) in water (46 mL) were added gradually (N,N-diethylacrylamide over 5 h and ammonium persulphate over 6 h) and continued to stir at 70° C. for additional 2 h after the persulphate addition was complete.

The precipitated copolymer was separated from the reaction mixture by decantation and it was redissolved in distilled water to make 20% clear and pale yellow colored solution that had the viscosity of 480 cps at 25° C.

It showed the LCST of 30-32° C. Yield 410.0 g. The intrinsic viscosity was determined by Ubbelohde viscometer. The weight average molecular weight of copolymer ($k=9.59 \times 10^{-3}$ and $a=0.65$) was found to be $5.53 \times 10^4$ grams/mole. $E^{1\%}_{cm}$ was found to be 26 at $\lambda_{max}$ 310 nm.

IR and NMR analysis of the dried sample is as follows:
IR: 1631 cm$^{-1}$, 2974 cm$^{-1}$ and 3296 cm$^{-1}$ $^1$H NMR (400 MHz, DMSO-d$_6$): δ broad signal at 0.79, 0.88, 1.04, 1.10, 1.18, 1.44, 1.91, 3.22, 4.47, 5.47 and 7.45.

Example IV

Copolymerization of N-Isopropyl Acrylamide and p-Methoxy Cinnamido Propyl, p-Vinyl Benzyl Dimethyl Ammonium Chloride (m:n::40:4)

A mixture of p-methoxy cinnamido propyl p-vinyl benzyl dimethyl ammonium chloride, 30% solution from step (a) (54.0 g, 39.13 mmol), N-isopropyl acrylamide (9.08 g, 80.31 mmol) (20% of total) and water (90 mL) was stirred at 80-82° C. under nitrogen blanket.

To the above preheated and stirred solution, N-isopropyl acrylamide (36.25 g, 320.38 mmol) (80% of total) in water (90 mL) and ammonium persulphate (4.23 g, 18.54 mmol) in water (45 mL) were added gradually (N-isopropyl acrylamide over 5 h and ammonium persulphate over 6 h) and continued to stir at 80-82° C. for additional 2 h after the persulphate addition was complete.

The precipitated copolymer was separated from the reaction mixture by decantation and it was redissolved in distilled water to make 20% clear and pale yellow colored solution that had the viscosity of 260 cps at 25° C.

It showed the LCST of 34-36° C. Yield 300.0 g. The intrinsic viscosity was determined by Ubbelohde viscometer. The weight average molecular weight of copolymer ($k=9.59 \times 10^{-3}$ and $a=0.65$) was found to be $5.41 \times 10^4$ grams/mole. $E^{1\%}_{cm}$ was found to be 82 at $\lambda_{max}$ 310 nm IR and NMR analysis of the dried sample is as follows:
IR: 1626 cm$^{-1}$, 2975 cm$^{-1}$, 3282 cm$^{-1}$. $^1$H NMR (400 MH&, DMSO-d6): δ broad signal at 1.04, 1.46, 1.96, 3.17, 3.82, 4.14, 7.34.

Example V

Preparation of Cream with Copolymer of Example I

| Ingredients | Trade Name | Weight % |
|---|---|---|
| Phase A | | |
| Water (Aqua) | | q.s. to 100 |
| Carbomer | Carbopol 940 | 00.60 |
| Titanium dioxide | | 00.50 |
| Propylene Glycol | | 10.00 |
| EDTA disodium | | 00.10 |
| Phase B | | |
| Glycerol Mono Stearate | | 02.00 |
| Cetostearyl alcohol | | 05.00 |
| Stearic acid | | 01.00 |
| Ceteth-20 | | 00.50 |
| Phase C | | |
| Copolymer of Example I | | 05.00 |
| Phenoxyethanol, Capryloyl Glycine and Undecylenoyl Glycine | Galguard Trident | 01.20 |
| Cyclopentasiloxane & Dimethicone Crosspolymer | DOWSIL ™ 9040 | 01.00 |
| Cyclomethicone | | 03.00 |
| Fragrance & Color | | q.s |

Carbopol 940 powder is dispersed in calculated amount of water and allowed it to soak for a two hrs. Thereafter all the ingredients of Phase A (aqueous phase) are added and the mixture is stirred to get uniform dispersion with TiO$_2$ (TiO$_2$ is initially dispersed in calculated amount of propylene glycol before adding) and heated to 75° C., All the ingredients of Phase B (oil phase) are mixed in a separate vessel and heated to 75° C., and Phase B is added to stirred Phase A over period of 10 minutes. Both Phase A and Phase B are homogenized together at 5000 rpm for 5 minutes. The mixture is cooled down to room temperature and then Phase C is added under stirring. The pH of the cream formulation is adjusted to 5.5 with 50% citric acid solution. The cream thus prepared has viscosity of 23,000 cps.

Example VI

Preparation of Spray Formulation with Copolymer of Example I

| Ingredients | Trade Name | Weight % |
|---|---|---|
| Phase A | | |
| Water (Aqua) | | q.s. to 100 |
| Acrylates/C10-30 Alkyl Acrylate Crosspolymer Carbopol | Ultrez-20 Polymer | 00.10 |
| Propylene Glycol | | 05.00 |
| EDTA tetra sodium | | 00.10 |
| Phase B | | |
| Glycerol Mono Stearate | | 02.00 |
| Cetostearyl alcohol | | 00.50 |
| Caprylic/Capric Triglyceride | GalMOL CCT | 02.00 |
| Ceteth-20 | | 01.00 |
| Phase C | | |
| copolymer of Example I | | 05.00 |
| Phenoxyethanol (and) Capryloyl Glycine (and) Undecylenoyl Glycine | Galguard Trident | 01.20 |
| Dimethicone | | 02.00 |
| Fragrance & Color | | q.s |

Carbopol Ultrez-20 powder is dispersed in calculated amount of water. All ingredients of Phase A (Aqueous phase) are added together and mixed at 70° C. till the uniformity is achieved. Similarly, Phase B is made separately and stirred to 75° C. for 10 mins. Phase B was then gradually added to Phase A and the mixture is homogenized at 5000 rpm for five minutes using a high shear homogenizer. The mix is cooled under stirring to 25° C. and Phase C is added under stirring. The pH of the mix is adjusted to 5.8 with citric acid solution. It is a thin liquid with haze.

Example VII

Preparation of a Sunscreen Formulation without Copolymer of Example II

| Ingredients | Weight % |
|---|---|
| Phase A | |
| Water | To make 100 |
| Xanthan Gum | 0.8 |
| TiO$_2$ | 0.7 |
| Propylene Glycol | 10 |
| Phase B | |
| Octyl methoxy cinnamate | 6 |
| Avobenzone | 2 |
| Cetostearyl Alcohol | 4 |
| Glyceryl Mono stearate | 2 |
| Stearic Acid | 1 |
| Ceteth-20 | 0.5 |
| Phase C | |
| Dowsil 9040 Silicone Elastomer Blend | 4 |
| Cyclomethicone | 5 |
| Galgaurd Trident | 1 |
| pH | 5.5-5.8 |

Example VIHI

Preparation of a Cream Formulation with Copolymer of Example II

| Ingredients | Weight % |
|---|---|
| Phase A | |
| Water | To make 100 |
| Xanthan Gum | 0.8 |
| Carbopol 940 | — |
| TiO$_2$ | 0.7 |
| Propylene Glycol | 10 |
| Phase B | |
| Octyl methoxy cinnamate | 6 |
| Avobenzone | 2 |
| Cetostearyl Alcohol | 4 |
| Glyceryl Mono stearate | 2 |
| Stearic Acid | 1 |
| Ceteth-20 | 0.5 |
| Phase C | |
| Dowsil 9040 Silicone Elastomer Blend | 4 |
| Cyclomethicone | 5 |
| Polymer of Example II | 10 |
| Galgaurd Trident | 1 |
| pH | 5.5-5.8 |

The present invention is not to be limited in scope by the specific embodiments described herein. Indeed, various modifications of the invention, in addition to those described herein, will become apparent to those skilled in the art from the foregoing description and accompanying figures. Such modifications are intended to fall within the scope of the appended claims. The invention is, therefore, to be limited only by the terms of the appended claims along with the full scope of equivalents to which the claims are entitled.

We claim:

1. A process to produce stimuli responsive UV absorbing water-soluble polymers of Formula I;

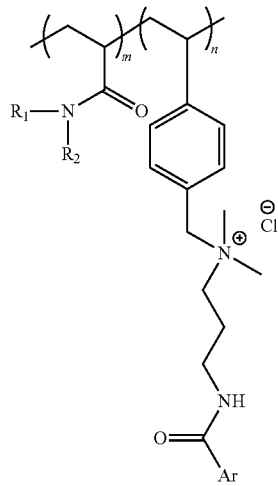

Formula I wherein, ArCO is an UV absorbing moiety selected from 2-cyano-3,3-diphenyl acryloyl and p-methoxy cinnamoyl, $R_1$ is selected from H and $C_1$-$C_3$ alkyl group and $R_2$ is selected from $C_1$-$C_3$ alkyl group, n and m are integers for the moles of monomers and a ratio of m t on is 40:5 to 40:1, and the process comprises a) synthesizing of monomers (Formula IV), by quaternization of corresponding tertiary amines (Formula II) with p-vinyl benzyl chloride (Formula III), in aqueous medium; and

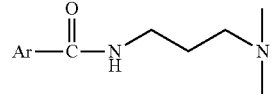

Formula II

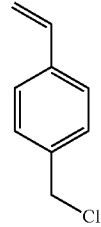

Formula III

-continued

Formula IV

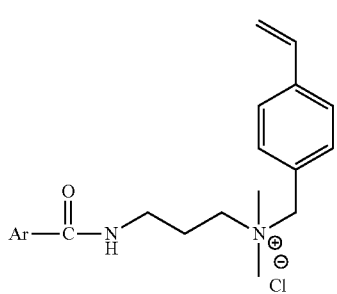

b) copolymerizing in aqueous medium using water-soluble radical initiators and monomers (Formula IV) of step (a) with N-substituted acrylamides (Formula V)

Formula V

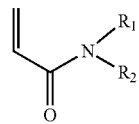

wherein $R_1$ is selected from H and $C_1$-$C_3$ alkyl group and $R_2$ is selected from $C_1$-$C_3$ alkyl group, wherein aqueous solution of compound of Formula V (60-90% of total by weight) and water-soluble radical initiator are gradually added simultaneously to a stirred and preheated aqueous solution of compound of Formula IV and compound of Formula V (10-40% of the total) under nitrogen over a period of time.

2. The process as claimed in claim 1, wherein the amount of water-soluble radical initiators used in step (b) is 1.0%-10% by weight based on the concentration of monomers of Formula IV and Formula V.

3. The process as claimed in claim 1, wherein the compound of Formula II is p-methoxy cinnamido propyl dimethyl amine, and the compound of Formula IV is p-methoxy cinnamido propyl p-vinyl benzyl dimethyl ammonium chloride.

4. The process as claimed in claim 1, wherein the compound of Formula II is 2-cyano-N-(3-(dimethylamino) propyl)-3,3-diphenylacrylamide, and the compound of Formula IV is 2-cyano-3,3-diphenyl acrylamido propyl p-vinyl benzyl dimethyl ammonium chloride.

* * * * *